United States Patent [19]

Lemler et al.

[11] Patent Number: 5,725,377
[45] Date of Patent: Mar. 10, 1998

[54] DENTAL IMPLANT APPARATUS

[76] Inventors: Jeffrey Richard Lemler, 2 Bobby Close, Mamaroneck, N.Y. 10543; Seymour Saslow, 199 Caroline St., Saratoga Springs, N.Y. 12866-3414

[21] Appl. No.: 625,047

[22] Filed: Mar. 29, 1996

[51] Int. Cl.⁶ .................................................. A61C 8/00
[52] U.S. Cl. ................................. 433/173; 433/201.1
[58] Field of Search .......................... 433/172, 173, 433/174, 175, 176, 201.1

[56] References Cited

U.S. PATENT DOCUMENTS

| | | | |
|---|---|---|---|
| 4,027,392 | 6/1977 | Sawyer et al. | 32/10 A |
| 4,175,565 | 11/1979 | Chiarenza et al. | 433/32 |
| 4,195,367 | 4/1980 | Kraus | 3/1.91 |
| 4,856,994 | 8/1989 | Lazzara et al. | 433/173 |
| 5,037,442 | 8/1991 | Wintermantel et al. | 623/23 |
| 5,145,371 | 9/1992 | Jorneus | 433/173 |
| 5,145,372 | 9/1992 | Daftary et al. | 433/173 |
| 5,292,252 | 3/1994 | Nickerson et al. | 433/173 |

OTHER PUBLICATIONS

Brighton et al In Vitro Bone–Cell Response to a Capacitively Coupled Field, Clinical Orthopaedics and Related Research, Section III Basic Science and Pathology, pp. 255–262 (No. 285, Dec. 1992).

Fitzsimmons et al, Frequency Dependence of Increased Cell Proliferation, In Vitro, In Exposures to a Low–Amplitude, Low Frequency Electric Field: For Dependence on Increased Mitogen Activity Released Into Culture Medium, Journal of Cellular Physiology, pp. 586–591 (1989).

Friedenberg, et al, The Effects of Demineralized Bone Matrix and Direct Current on an "In Vivo" Culture of Bone Marrow Cells, Journal of Orthopaedic Research, pp. 22–27, vol. 7, No. 1, 1989.

Friedenberg, et al, Bone Reaction to Varying Amounts of Direct Current, Surgery, Gynecology, and Obstetrics Nov., 1970, pp. 894–899.

Ohashi, Electrical Callus Formation and its Osteogenesis, Journal Orthopaedic Association, vol. 59, 1982, pp. 37–55.

Kubota, et al. Overview of Effects of Electrical Stimulation on Osteogensis and Alveolar Bone, Journal of Periodontics, Jan., 1995, vol. 66, No. 1, pp. 1–6.

Steiner, et al. Electrical Stimulation of Bone and Its Implications for Endosseous Dental Implantation, Journal of Oral Implantology, vol. 26, No. 1, 1990, pp. 20–27.

*Primary Examiner*—Nicholas D. Lucchesi
*Attorney, Agent, or Firm*—Weingram & Associates P.C.

[57] ABSTRACT

A dental implant employs electrical bone growth stimulation by incorporating a galvanic cell in the implant. The implant is formed as a machine screw made of titanium. The machine screw contains an internal threaded portion for accommodating a cap screw to cover the top of the implant. Within the hollow portion is pressed a small aluminum rivet which makes intimate contact with the titanium implant. This forms the anode of the cell which will become the negative electrode of the battery. A slug of silver chloride is fastened to a cover screw. A saline solution is used as the electrolyte. Once activated, the reaction consists of the reduction of silver chloride to metallic silver. The slug of silver chloride forms the cathode of the cell and becomes the positive terminal of the battery.

30 Claims, 4 Drawing Sheets

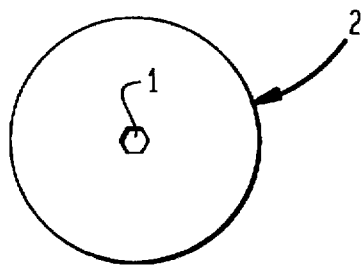
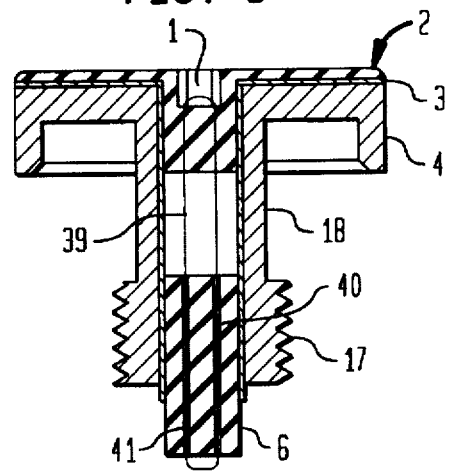
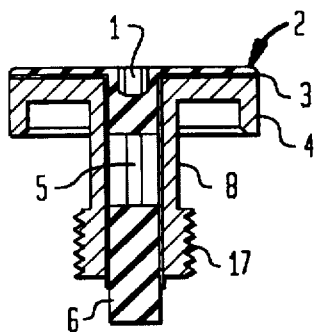
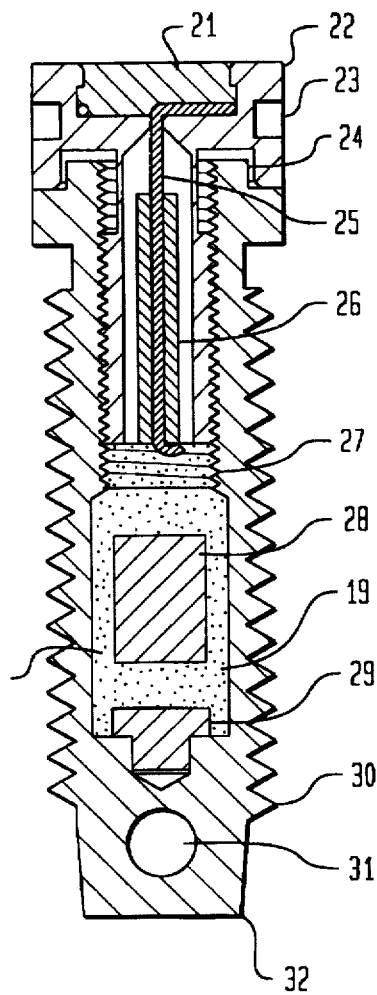
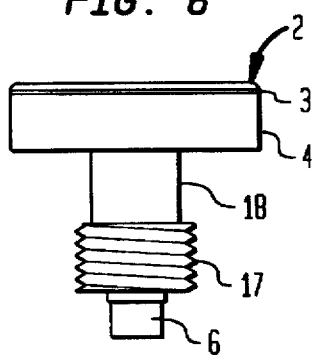

DENTAL IMPLANT APPARATUS

BACKGROUND OF THE INVENTION

1. Field of the Invention

The present invention relates to an electrical bone growth stimulator which is surgically inserted as a dental implant to accelerate and enhance the initial and the primary healing of the bone that surrounds the implant surgical site.

2. Description of the Related Art

U.S. Pat. No. 5,292,252 to Nickerson et. al. discloses a stimulator healing cap for enhancing and speeding the growth of bone cells and bone tissue surrounding a dental implant. The stimulating healing cap includes a threaded portion which is engageable with an interior threaded portion of the implant and a top portion containing a current source. The top portion and the threaded portion may be conductive and are connected by a middle insulated portion. The threaded portion is coupled to one pole of the current source and the top portion is coupled to the other pole of the current source. The latter current source maybe coupled to a coil wound around a longitudinal core inside the threaded portion. The stimulated healing cap provides a current path in the vicinity of bone tissue surrounding the implant to stimulate the growth of bone tissue and speed the primary healing phase after the implant is surgically inserted.

Sawyer, et al. U.S. Pat. No. 4,027,392 discuss the work of Linkow and others on methods and apparatus for dental implantation and prosthetic tooth forms that accompany those methods. The patent also discusses electrical bone growth stimulation. The patent proposes an implant which contains or may be connected to a source of electrical power to generate an electric current between an implant portion implanted in bone which serves as one electrode and a cap or crown which serves as the second electrode. Various alternative sources of power are proposed in this patent.

Kraus, U.S. Pat. No. 4,195,367, shows a ceramic tooth prosthesis which has a magnetic core embedded therein. A coil winding is embedded in the jaw bone.

Lazzara, et al. U.S. Pat. No. 4,856,994 show a dental implant structure in which cooperation of a healing cap permits use without stressing the underlying dental implant.

Wintermantel, et al. U.S. Pat. No. 5,037,442 relates to a fixing stem for a prosthesis which is implanted in a surgically prepared bone cavity and subsequently removed without damage with the prosthesis stem or the bone cavity.

Jorneus, U.S. Pat. No. 5,145,371 relates to a structure for an insert into a fixture of a dental implant. The insert is designed to provide very short height for a dental bridge above the fixture.

Daftary, et al. U.S. Pat. No. 5,145,372 show a special healing cap which consists of several parts affixed to the insert of various dental implants.

Chiarenza, et al. U.S. Pat. No. 4,175,565 disclose a dental implant and propose an electrical current be generated at the implant between the implant and a second electrode affixed to the patient's skin preferably at the ear.

SUMMARY OF THE INVENTION

The present invention is directed to a dental implant employing a battery constructed within it. The battery employs a first silver chloride electrode and a second aluminum electrode.

Two embodiments of the invention are disclosed. In the first embodiment (FIGS. 1–8), the implant is formed as a machine screw made of titanium. The machine screw contains an internal threaded portion for accommodating a cap screw to cover the top of the implant. Within the hollow portion is pressed a small aluminum rivet which makes intimate contact with the titanium implant. This forms the anode of the cell which will become the negative electrode of the battery.

A cylindrical slug of silver chloride is fastened to a cover screw by means of fine silver wire which is threaded through two holes in the slug and returning through a center hole in the cover screw. The wire is insulated from the screw as it passes out to the top and holds the slug in position. The chloride on the outer surface of the slug is reduced with a photographic reducing agent such as elon developer forming a skin of coherent metallic silver over the surface. The skin is semipermeable and permits penetration of electrolyte to the unreacted silver chloride material. The skin provides a current collecting member during the initial stages of activation. A saline solution is used as the electrolyte. Once activated, the reaction consists of the reduction of silver chloride to metallic silver. The slug of silver chloride forms the cathode of the cell and becomes the positive terminal of the battery. It retains its original shape and structural strength as battery life progresses. The screw forms the aluminum anode and remains clean during the life of the cell. An insulated gold surface on the cover serves as the positive battery contact.

The second embodiment is described in FIGS. 9–15. The second embodiment is similar to first embodiment in that the dental implant portion is a threaded titanium machine screw. However, the second embodiment contains a larger hollow space therein for electrolyte and modifies the configuration of the rivet which is surrounded by the electrolyte so that the amount of electrolyte is increased and the surface area of the rivet in contact with the electrolyte is increased for reaction with the electrolyte. Additionally, we have discovered that the electrolyte, the reaction, and the battery life are increased when a fibrous organic filler such as absorbent paper is placed in the space housing the electrolyte. While the reasons for the improvements obtained with the fibrous organic filler are not clear, it appears that the filler absorbs some of the electrolyte solution thereby controlling the reaction time and acting as an accumulator.

It is also observed in this embodiment magnesium may be employed instead of an aluminum rivet so as to increase the EMF output of the battery.

Silver chloride surrounds a silver wire conductor which runs from the underside of the cap screw base around a silver resin filler therein to contact the open space in the saline electrolyte.

The cap screw in the second embodiment is formed of high temperature resistant plastic known as DORLAN sheet. The cap screw contains a silver filler portion at the top thereof so that holes are provided in the cap screw for use by a wrench to lock the screw in place and to remove same. A seal of silicon rubber is provided between the cap screw and the implant base and a thin film of silicon rubber which acts as a gasket seal.

A principal object and advantage of our invention is the provision of a dental implant which incorporates electrical bone growth stimulation where the electrical current is generated by a galvanic cell formed in the implant. Another object and advantage of our invention is the provision of an electrical bone growth stimulator having an anode and a cathode where the anode is formed in the implant and the cathode is formed in the cap. A still further object and advantage of the invention is the provision of a battery in a dental implement which battery employs a silver chloride electrode and an aluminum electrode.

Another object and advantage of the invention is the provision of an dental implant where the anode of the battery is formed within a hollow portion of the dental implant. A still further object and advantage of the invention is the provision of a battery in a dental implant which incorporates a first silver chloride electrode and a second aluminum electrode. Another object and advantage of the invention is the provision of a dental implant which incorporates a galvanic cell having a saline solution therein as the electrolyte. A still further object and advantage of the invention is the provision of a dental implant with electrical bone growth stimulation where the battery can be easily changed.

Another object and advantage of the invention is the provision of a cylindrical slug of silver chloride fastened to a cover screw. A still further object and advantage of the invention is fastening the silver chloride to the cover screw by means of fine silver wire which is threaded through two holes in the slug and returning through a center hole in the cover screw. A still further object of the invention is the provision of a dental implant where the wire is insulated from the screw as it passes out of the top and holds the slug in position.

A still further object and advantage of the invention is the provision whereby chloride on the outer surface of the slug is reduced with a photographic reducing agent such as elon developer to form a skin of coherent metallic silver over the surface. Another object and advantage of the invention is the provision of a skin which is semipermeable to permit penetration of electrolyte to the unreacted silver chloride material. A still further object and advantage of the invention is the provision of a skin for current collecting during the initial stages of activation. Another object and advantage of the invention is the provision of a saline solution as the electrolyte.

Another object and advantage of the invention is the provision of a battery in a dental implant stimulator where the reaction consists of the reduction of silver chloride to metallic silver. Another object and advantage of the invention is the provision of a battery for a dental implant where a slug of silver chloride forms the cathode of the cell and becomes the positive terminal of the battery. Another object of the invention is the provision of a cathode which retains its original shape and structural strength as battery life progresses. A still further object and advantage of the invention is the provision of a battery in a dental implant where the cap screw of the implant forms the aluminum anode and remains clean during the life of the cell. A still further object and advantage of the invention is the provision of a dental implant having an insulated gold surface on the cover screw cap forming the positive battery contact.

BRIEF DESCRIPTION OF THE DRAWINGS

FIG. 5 is a sectional view of the cap portion of the invention shown in FIG. 1;

FIG. 6 is a side view of the portion of the invention shown in FIG. 5;

FIG. 7 is a top view of the portion of the invention shown in FIG. 6;

FIG. 8 is a side view of a portion of the invention showing an alternate structure for fastening the silver chloride to the cover screw;

FIG. 9 is a side view, in section, of the second embodiment of the dental implant in accordance with our invention;

DETAILED DESCRIPTION OF THE PREFERRED EMBODIMENTS

Figure 1:
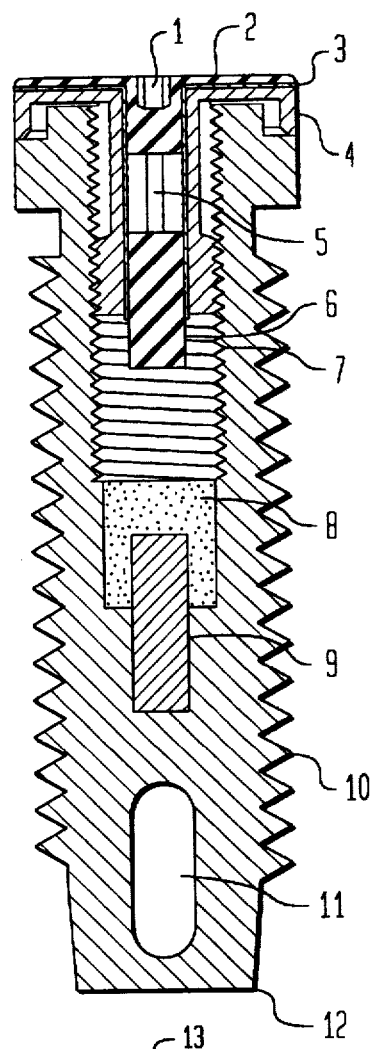
FIG. 1 is a side view, partially in section, of one embodiment of the dental implant in accordance with our invention.

As shown in FIGS. 1–8, the dental implement includes a threaded body portion and a cap portion. The body has a threaded cavity formed therein for receiving and forming a portion of a galvanic cell and for supporting the cap portion. The dental implant includes a slot 1 formed in the top cap 2. The top cap 2 is electrically insulated at 3 from the threaded body section 4 of the top of the screw. A rod 5, which is electrically conductive, supports and is connected to the first part of the battery namely the silver chloride section 6. The rod 5 electrically is a resistance.

The implant body 12 has an aperture 11 formed therein for achieving bone growth therethrough. The implant body 12 is threaded at 10 for aiding the engagement of the bone. Mounted in the implant portion is the aluminum section of the battery 9. This is surrounded by electrolyte 8 in a cavity formed in implant 12.

Figure 2:
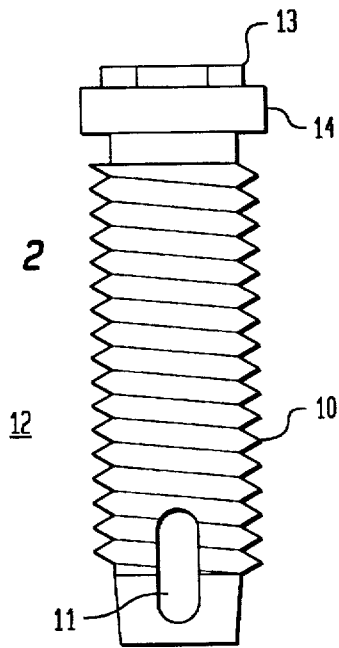
FIG. 2 is a side view of the body portion of the embodiment of FIG. 1.

The various components of the combination shown in FIG. 1 are described in greater detail in FIGS. 2–8. FIG. 2, a sideview of the titanium screw threaded dental implant body 12, shows the aperture 11 therein near the base of the implant. Threads 10 are provided to aid in securing the implant to the bone. Aperture 11 is provided to enhance growth of bone through the aperture to properly secure the implant in the jaw bone. The implant 12, at its upper end, has an end cap hex 13 formed on the rim 14 of the body 12.

Figure 4:
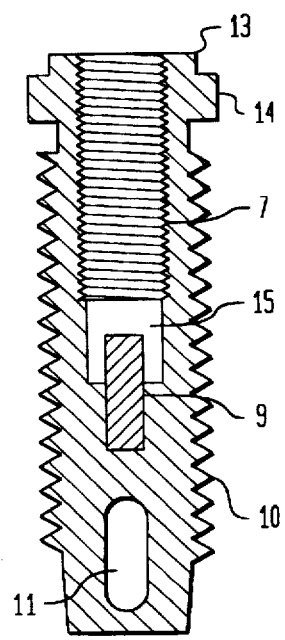
FIG. 4 is a cross-section view of the portion of the invention shown in FIG. 2.

FIG. 4 is a sectional view taken along a line drawn in the center of the device shown in FIG. 2. FIG. 4 shows the internal threads 7 which are formed centrally and axially through the body 12. A cavity 15 is formed beneath the screw threads 7 within the implant body 12. This cavity has one battery element 9 electrically connected to the body 12 by intimate contact.

Figure 3:
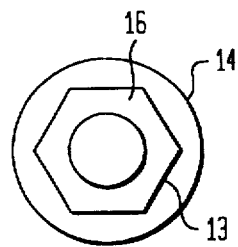
FIG. 3 is a top view of the portion of the invention shown in FIG. 2.

As shown in FIG. 3, the body 12 of FIGS. 2 and 4 has a central aperture 16 formed from approximately the location of the battery element 9 up to and through the end hex 13 of the implant. A sealing cap which mounts in and threadedly engages the body 12 shown in FIGS. 5, 6, and 7.

FIG. 7 is a top view of the end cap. This shows a small hex nut aperture 1 for tightening the cap. The cap as shown in FIG. 7 has a top surface portion 2. FIG. 6 is a side view of the cap. The upper surface portion 2 which is described in connection of FIG. 1 is electrically insulated 3 from base of the cap 4. The base of the cap 4 has a cylinder 18 extending therefrom. A portion of the cylinder 18 is threaded at 17.

FIG. 5 is a sectional view taken along the center line of FIG. 6. Mounted within the cylinder 18 is the rod 5 and battery element 6 described in connection with FIG. 1.

FIG. 8 is a side view showing an alternate for fastening the cylindrical slug of silver chloride to the cover screw. In this embodiment, the rod 5 is eliminated and slug 6 is fastened to the cover 2 screw by means of fine silver wire 39 which is threaded through two holes 40 and 41 in the slug 6 and returning to the center hole 1 in the cover screw 2. The wire is insulated from the screw as it passes out to the top and holds the slug in position. The chloride on the outer surface of the slug is reduced with a photographic reducing agent such as elon developer forming a skin of coherent metallic silver over the surface. The skin is semipermeable and permits penetration of electrolyte to the unreacted silver chloride material. The skin provides a current collecting member during the initial stages of activation.

As shown in FIGS. 9-15, the second embodiment of our dental implement also includes a threaded body portion and a cap portion. Like the first embodiment, the body has a threaded cavity formed therein for receiving and forming a portion of a galvanic cell and for supporting the cap portion. The dental implant of FIGS. 9-15, differs from the embodiment of FIGS. 1-8 in several respects. The embodiment of FIGS. 9-15 has a large cavity 20 for increasing the volume of electrolyte 19 used in the galvanic cell. The implant body 32 includes a slug of resin 21 (70% silver filled) in the cap screw 22. The cap screw 22 has holes 23 formed laterally therein for assisting in removal and tightening of the screw with the aid of a tool such as a wrench.

The bottom of the cap screw 22 is sealed from the top of the body 32 with a thin film of silicon rubber thus forming a gasket seal. A silver wire conductor 25 is wrapped around the base of the slug 21 and is connected centrally of the implant downward to the top of the electrolyte cavity 20. The wire 25 is surrounded by silver chloride 26.

The cap screw 22 threadedly engages the interior threads 27 of the body 32. We have found that used of a fibrous organic filler 28 in the electrolyte 19 enhances the output of the galvanic cell by acting as an accumulator. The other pole 29 of the cell is a rivet 29 pressed into the bottom of the cavity 20. The rivet 29 is shaped to present a larger surface area to the electrolyte 19 than the rivet 9 in FIG. 1. The rivet may be made of either aluminum or magnesium. Magnesium will produce a higher voltage than aluminum.

The implant body of FIG. 9 includes external threads 30 and a circular aperture 31 to secure the implant to the bone and to provide a path for bone growth through the implant body, respectively. The electrolyte 19 is a saline solution.

Figure 10:
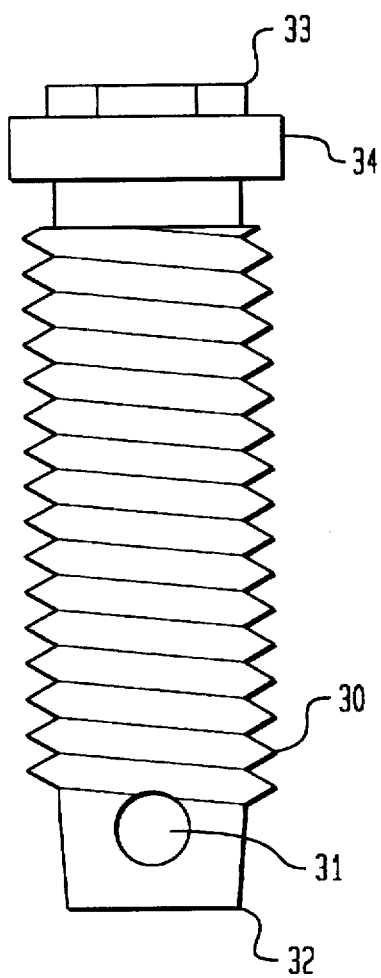
FIG. 10 is a side view of the body portion of the second embodiment of out invention shown in FIG. 9.

The various components of the combination shown in FIG. 9 are described in greater detail in FIGS. 10-15. FIG. 10, a side view of the titanium screw threaded dental implant body 32 shows the aperture 31 therein near the base of the implant. Threads 30 are provided to aid in securing the implant to the bone. Aperture 31 is provided to enhance growth of bone through the aperture to properly secure the implant in the jaw bone. The implant 32, at its upper end, has an end cap hex 33 formed on the rim 34 of the body 32.

Figure 12:
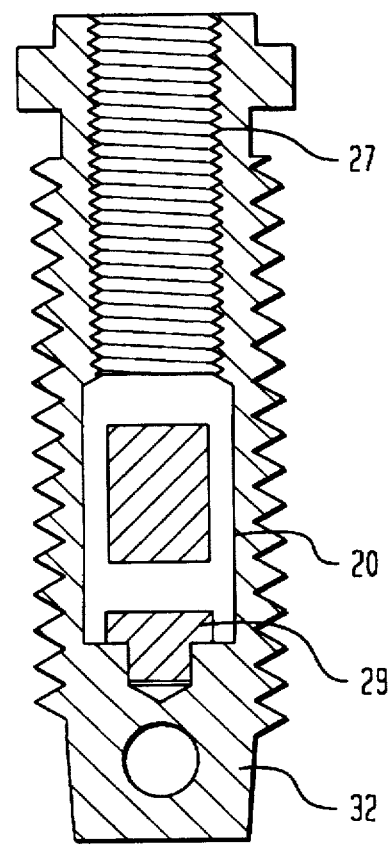
FIG. 12 is a cross-section view of the portion of the invention shown in FIG. 11.

FIG. 12 is a sectional view taken along a line drawn in the center of the device shown in FIG. 10. FIG. 12 shows the internal threads 27 which are formed centrally and axially through the body 32. A cavity 20 is formed beneath the screw threads 27 within the implant body 32. This cavity 20 has one battery element 29 electrically connected to the body 32 by intimate contact.

Figure 11:
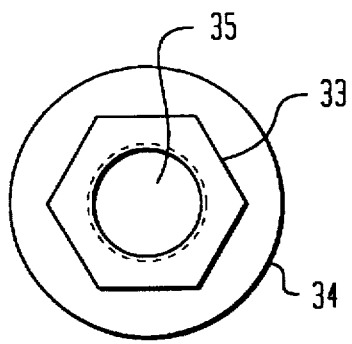
FIG. 11 is a top view of the portion of the invention shown in FIG. 10.

As shown in FIG. 11, the body 32 of FIGS. 10 and 12 has a central aperture 35 formed from approximately the location of the battery element 29 up to and through the end hex 33 of the implant.

Figure 15:
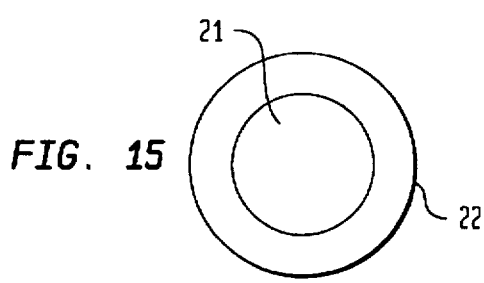
FIG. 15 is a top view of the portion of the invention shown in FIG. 14.
Figure 14:
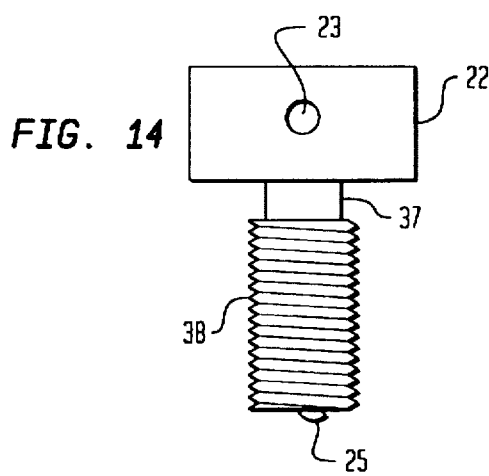
FIG. 14 is a side view of the cap portion of the invention shown in FIG. 13.
Figure 13:
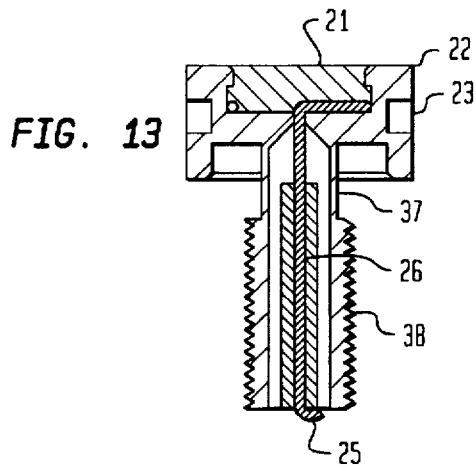
FIG. 13 is a sectional view of the cap portion of the embodiment of our invention shown in FIG. 9.
Figure 16:
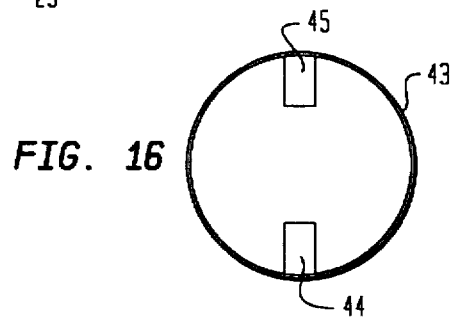
FIG. 16 is a top view of an alternate cap structure.
Figure 17:
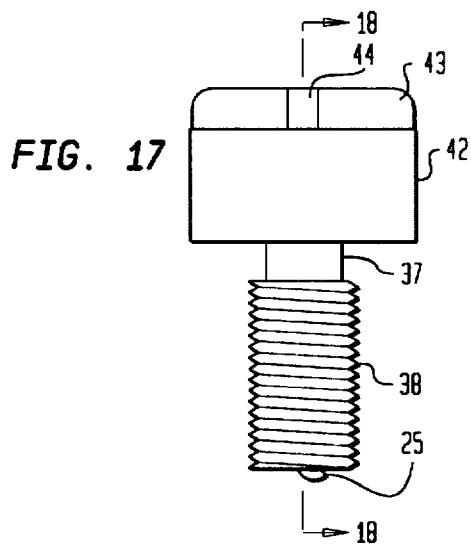
FIG. 17 is a side view of the alternate cap of FIG. 16.
Figure 18:
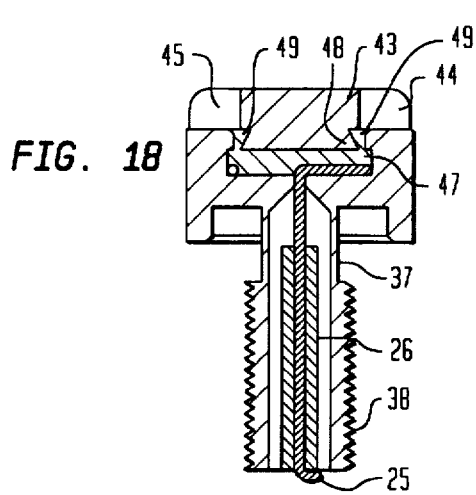
FIG. 18 is a sectional view of the alternate cap of FIGS. 16–17.

A sealing cap which mounts in and threadedly engages the body 32 is shown in FIGS. 13, 14 and 15. The end cap shown in FIGS. 13-15 includes a cap 22 with a slug of silver resin 21 impressed therein. The base of the cap 22 has a cylinder 37 extending from its base. A portion of the cylinder 37 is externally threaded at 38. A wire 25 is connected between the slug 21 and the end of the threaded cylinder 37. The wire is surrounded by silver chloride 26.

Another sealing cap for mounting in and threadedly engaging the body 32 is described in FIGS. 16-19. Here, the cap has a body portion 42 of a plastic such as DORLAN. A slug of silver chloride resin 47 is held in place by a titanium cover 43. The titanium cover 43 has two slots, 44 and 45 formed therein. The slots are provided so that the cap can be affixed to or removed from the base of the implant with the aid of a tool such as a wrench. The titanium cover 43 is provided with an angled protrusion 48. The dimensions of the protrusion 48 and the angled section 49 mechanically retain the cover 43 to the body 42 over the sliver chloride slug 47. The cover 43 is sealed to the body 42 with epoxy.

It will be apparent to those skilled in the art that the invention disclosed and claimed herein may also be utilized as an orthopedic appliance in bone attachment devices such as bone screws. In these applications, the battery unit may be sealed.

Further modifications to the method and apparatus of the invention may be made without departing from the spirit and scope of the invention; accordingly, what is sought to be protected is set forth in the appended claims.

What is claimed is:

1. A stimulator dental implant including a healing cap for enhancing in a patient the growth of bone cells and bone tissue surrounding said dental implant comprising:

a. a threaded open interior portion having a proximal opening adapted to be located near the gingival cortical plat interface in a patient;

b. a conductive first portion having a longitudinal axis which threads in and matingly engages in the open threaded interior portion of the implant wherein an unthreading of said conductive threaded first portion from the threaded open interior portion of the dental implant disengages said stimulator healing cap from the dental implant;

c. a galvanic cell formed in said implant; said galvanic cell including an anode formed in said threaded open interior portion and a cathode formed in said conductive first portion, said anode including a small aluminum rivet in intimate contact with said threaded portion and said cathode including a cylindrical slug of silver chloride fastened to said conductive first portion; and an electrolyte solution in said open interior portion between said anode and said cathode.

2. A dental implant including a stimulator healing cap for enhancing in a patient the growth of bone cells and bone tissue surrounding said dental implant comprising:

a. a threaded open interior portion having a proximal opening adapted to be located near the gingival cortical plat interface in a patient;

b. a conductive first portion having a longitudinal axis which threads in and matingly engages in the open threaded interior portion of the implant wherein an unthreading of said conductive threaded first portion from the threaded open interior portion of the dental implant disengages said stimulator healing cap from the dental implant;

c. a battery formed in said implant between said threaded open in interior portion and said conductive first portion, said battery including an anode formed said threaded open interior portion and a cathode formed in said conductive first portion, said anode being composed of aluminum in intimate contact with said threaded portion, said cathode being composed of silver chloride fastened to said conductive first portion; and a saline solution electrolyte.

3. In a dental implant including an electrical stimulator healing cap for enhancing in a patient the growth of bone cells and bone tissue surrounding said dental implant, the implant having a titanium implant portion and a gold cap portion, a battery formed in said implant comprising: an anode formed in said titanium implant portion and a cathode formed in said gold cap portion, said anode being composed of aluminum in intimate contact with said titanium portion, said cathode being composed of silver chloride fastened to said gold cap portion; and an electrolyte composed of a saline solution between said anode and said cathode.

4. The battery of claim 3 wherein said anode includes an aluminum rivet.

5. The battery of claim 3 wherein said cathode includes a cylindrical slug of silver chloride fastened to said cap portion.

6. The battery of claim 5 wherein said slug of silver chloride is fastened to said cap portion by fine silver wire.

7. The battery of claim 6 wherein said silver wire is electrically insulated from said cap portion.

8. The battery of claim 7 wherein silver chloride on the outer surface of said slug is reduced with a photographic reducing agent thereby forming a skin of coherent metallic silver over said outer surface.

9. The battery of claim 6 wherein silver chloride on the outer surface of said slug is reduced to form a semipermeable skin to enable penetration of said electrolyte for providing a current collecting means during the initial stages of activation.

10. The battery of claim 3 wherein a reaction in said battery consists of the reduction of silver chloride to metallic silver.

11. The dental implant of claim 3 wherein said cap portion includes an insulated gold surface forming a positive battery contact.

12. An electrical bone growth stimulator dental implant for enhancing in a patient the growth of bone cells and bone tissue comprising: an implant having a titanium implant portion and a gold cap portion, a battery formed in said implant having an anode formed in said titanium implant portion and a cathode formed in said gold cap portion, said anode being composed of aluminum in intimate contact with said titanium implant portion and said cathode being composed of silver chloride fastened to said gold cap portion; and an electrolyte composed of a saline solution, between said anode and said cathode in said titanium implant portion.

13. An electrical bone growth stimulator dental implant for enhancing in a patient the growth of bone cells and bone tissue comprising: an implant having a titanium implant body portion having a chamber formed therein, a battery for said implant including an aluminum anode mounted in said chamber in intimate contact with said titanium implant body portion, a cathode composed of silver chloride mounted in said chamber, and an electrolyte composed of a saline solution located in said chamber between said anode and said cathode.

14. The battery of claim 13 wherein said anode includes an aluminum rivet.

15. The battery of claim 13 wherein said dental implant includes a cap portion for covering said chamber, and said cathode includes a cylindrical slug of silver chloride fastened to said cap portion.

16. The battery of claim 15 wherein said slug of silver chloride is fastened to said cap portion by fine silver wire.

17. The battery of claim 16 wherein said silver wire is electrically insulated from said cap portion.

18. The battery of claim 17 wherein silver chloride on the outer surface of said slug is reduced with a photographic reducing agent thereby forming a skin of coherent metallic silver over said outer surface.

19. The battery of claim 16 wherein silver chloride on the outer surface of said slug is reduced to form a semipermeable skin to enable penetration of said electrolyte for providing a current collecting means during the initial stages of activation.

20. The battery of claim 13 wherein a reaction in said battery consists of the reduction of silver chloride to metallic silver.

21. The dental implant of claim 13 wherein said cap portion includes an insulated gold surface forming a positive battery contact.

22. A method of enhancing in a patient the growth of bone cells and bone tissue surrounding a dental implant comprising the steps of: forming a dental implant having a titanium implant portion intended to be implanted into bone tissue, forming a cavity in said titanium implant portion, fastening a first material in said cavity, filling said cavity with an electrolyte, forming a cap for sealingly engaging said titanium implant portion and closing said cavity, fastening a second material to said cap, sealingly engaging said cap and said implant portion to activate coaction between said first material, said electrolyte and said second material to produce an electrical charge about the surface of said implant portion to stimulate the growth of bone cells and bone tissue.

23. The method of claim 22 wherein said second material is silver chloride.

24. The method of claim 22 further including the step of placing a fibrous material in said electrolyte.

25. The method of claim 22 wherein said first material is aluminum.

26. The method of claim 22 wherein said first material is magnesium.

27. The method of claim 22 wherein said cap is plastic.

28. The method of claim 27 wherein said plastic is DORLAN.

29. The method of claim 22 wherein said electrolyte is a saline solution.

30. The method of claim 22 further including the step of sealing said cap and implant portion with epoxy.

* * * * *